United States Patent [19]

Lal et al.

[11] Patent Number: 4,590,197
[45] Date of Patent: May 20, 1986

[54] 9,10-SUBSTITUTED 2-MESITYLIMINO-3-ALKYL-3,4,6,7-TETRA-HYDRO-2H-PYRIMIDO(6,1-a)ISOQUINO-LIN-4-ONES, AND THEIR USE AS MEDICAMENTS

[75] Inventors: Bansi Lal; Alihussein N. Dohadwalla; Vijay A. Aroskar; Nandkumar K. Dadkar, all of Bombay, India; Horst Dornauer, Kelkheim, Fed. Rep. of Germany; Julius Mascarenhas; Noel J. deSouza, both of Bombay, India

[73] Assignee: Hoechst Aktiengesellschaft, Frankfurt, Fed. Rep. of Germany

[21] Appl. No.: 607,718

[22] Filed: May 7, 1984

[30] Foreign Application Priority Data

Sep. 10, 1981 [DE] Fed. Rep. of Germany ....... 3135831

Related U.S. Application Data

[63] Continuation of Ser. No. 415,837, Sep. 8, 1982, abandoned.

[51] Int. Cl.$^4$ .................. A61K 31/505; C07D 471/04

[52] U.S. Cl. .................. 514/267; 514/237; 544/119; 544/252
[58] Field of Search ............. 544/252, 119; 424/251, 424/248.56; 514/267, 237

[56] References Cited

U.S. PATENT DOCUMENTS

| 4,011,321 | 3/1977 | Coates et al. | 424/250 |
| 4,147,869 | 4/1979 | Nakagawa et al. | 544/363 |
| 4,210,753 | 7/1980 | Tominaga et al. | 544/128 |
| 4,400,506 | 8/1983 | Lal et al. | 544/246 |
| 4,482,556 | 11/1984 | Lal et al. | 424/251 |

FOREIGN PATENT DOCUMENTS

| 0075165 | 3/1983 | European Pat. Off. | 544/252 |
| 2470130 | 5/1981 | France . | |
| 0147624 | 5/1980 | India . | |
| 0149457 | 12/1981 | India . | |

Primary Examiner—Donald G. Daus
Assistant Examiner—Diana G. Rivers
Attorney, Agent, or Firm—Curtis, Morris & Safford

[57] ABSTRACT 9,10-substituted-2-mesitylimino-3-alkyl-3,4,6,7-tetrahydro-2H-pyrimido-(6,1-a)isoquinoline-4-ones and salts thereof having hypotensive and vasodilating properties.

8 Claims, No Drawings

9,10-SUBSTITUTED 2-MESITYLIMINO-3-ALKYL-3,4,6,7-TETRAHYDRO-2H-PYRIMIDO(6,1-a)ISOQUINOLIN-4-ONES, AND THEIR USE AS MEDICAMENTS

This application is a continuation of application Ser. No. 415,837, filed Sept. 8, 1982 now abandoned.

The invention relates to 9,10-substituted 2-mesitylimino-3-alkyl-3,4,6,7-tetrahydro-2H-pyrimido(6,1-a)isoquinolin-4-ones and their pharmaceutically tolerated salts, their preparation and their use as medicaments, in particular as hypotensive agents, and pharmaceutical formulations containing these compounds.

The compounds according to the invention are substituted 9-/10-alkoxy/(3'-substituted amino-2'-OR$^1$-propoxy)-2-mesitylimino-3-alkyl-3,4,6,7-tetrahydro-2H-pyrimido(6,1-a)isoquinolin-4-ones of the formula I

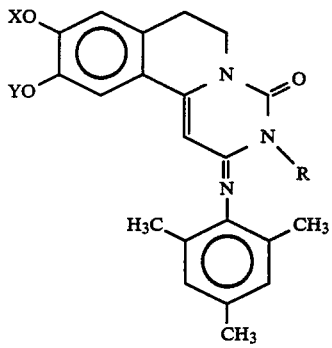

I in which R denotes straight-chain or branched $C_1$–$C_4$-alkyl and one of the radicals X and Y denotes straight-chain or branched $C_1$–$C_4$-alkyl and the other denotes —$CH_2CH(OR^1)CH_2NR^2R^3$, $R^1$, $R^2$ and $R^3$ being identical or different and denoting hydrogen or straight-chain or branched $C_1$–$C_4$-alkyl, or $R^2$ and $R^3$, together with the nitrogen atom to which they are bonded, denoting a heterocyclic ring which optionally contains a further nitrogen or oxygen atom and is optionally substituted, and their pharmaceutically tolerated salts.

Suitable $C_1$–$C_4$-alkyl groups for X, Y, R, $R^1$, $R^2$ and $R^3$ are methyl, ethyl, n-propyl, isopropyl, isobutyl or tert.-butyl. Suitable heterocyclic radicals containing nitrogen, —$NR^2R^3$, are, for example, piperidino, piperazino and morpholino, optionally substituted once or several times with $C_1$–$C_4$-alkyl, $C_2$–$C_5$-carboalkoxy such as, for example, carboethoxy, $C_7$–$C_9$-aralkyl such as, for example, benzyl, aryl such as, for example, phenyl which is optionally substituted once or several times with halogen such as fluorine or chlorine, or with $C_1$–$C_4$-alkoxy such as, for example, methoxy, or with trihalogeno-$C_1$–$C_4$-alkyl such as, for example, trifluoromethyl, or with hydroxyl or $C_1$–$C_4$-alkyl such as methyl or ethyl, or with a nitro group, or naphthyl or a heterocyclic radical such as, for example, pyridyl.

Examples of suitable salts of the 9-/10-alkoxy/(3'-subst. amino-2'-OR$^1$-propoxy)-2-mesitylimino-3-alkyl-3,4,6,7-tetrahydro-2H-pyrimido(6,1-a)isoquinolin-4-ones according to the invention which may be mentioned are salts with inorganic or organic acids, such as, for example, hydrochlorides, hydrobromides, hydriodides, sulfates, phosphates, acetates, propionates, oxalates, tartrates, citrates, maleates, fumarates, isethionates, succinates, pamoates, pivalates and the like.

Preferred substituents are: methyl or ethyl for R, straight-chain or branched $C_1$–$C_4$-alkyl for one of the two radicals X and Y and —$CH_2CH(OH)CH_2NR^2R^3$ for the other of the radicals X and Y, wherein $R^2$ denotes hydrogen and $R^3$ denotes straight-chain or branched $C_1$–$C_4$-alkyl or $R^2$ and $R^3$, together with the nitrogen atom to which they are bonded, denote a heterocyclic radical which optionally contains a further nitrogen atom or oxygen atom and is optionally substituted, in particular a piperidino, piperazino or morpholino radical, which is substituted as indicated above.

Particularly preferred compounds according to the invention are:

9-Methoxy-10-[3'-(4-phenylpiperazino)-2'-hydroxy-propoxy]-2-mesitylimino-3-methyl-3,4,6,7-tetrahydro-2H-pyrimido(6,1-a)isoquinolin-4-one dihydrochloride dihydrate.

9-Methoxy-10-[3'-(4-(2-pyridyl)-piperazino)-2-hydroxy-propoxy]-2-mesitylimino-3-methyl-3,4,6,7-tetrahydro-2H-pyrimido(6,1-a)isoquinolin-4-one trihydrochloride dihydrate.

9-Methoxy-10-[3'-(4-phenylpiperidino)-2'-hydroxy-propoxy]-2-mesitylimino-3-methyl-3,4,6,7-tetrahydro-2H-pyrimido(6,1-a)isoquinolin-4-one.

10-Methoxy-9-[3'-(4-phenylpiperidino)-2'-hydroxy-propoxy]-2-mesitylimino-3-methyl-3,4,6,7-tetrahydro-2H-pyrimido(6,1-a)isoquinolin-4-one dihydrochloride sesquihydrate.

Some of the new substituted 9-/10-alkoxy/(3'-subst. amino-2'-OR$^1$-propoxy)-2-mesitylimino-3-alkyl-3,4,6,7-tetrahydro-2H-pyrimido(6,1-a)isoquinolin-4-ones are listed in the following table.

| X | Y | Salt | Mp. (°C.) |
|---|---|---|---|
| $CH_3$ | $CH_2CHOHCH_2NHCHMe_2$ | 2 HCl | 246–248 |
| $CH_3$ | $CH_2CHOHCH_2NHCMe_3$ | 2 HCl | 237–239 |
| $CH_3$ | $CH_2CHOHCH_2$—$NHCH_2CHMe_2$ | 2 HCl·$H_2O$ | 228–229 |

The present invention further relates to a process for the preparation of the 9-/10-alkoxy/(3'-subst.amino-2'-OR$^1$-propoxy)-2-mesitylimino-3-alkyl-3,4,6,7-tetrahydro-2H-pyrimido(6,1-a)isoquinolin-4-ones of the formula I and their pharmaceutically tolerated salts which comprises allowing a compound of the formula II

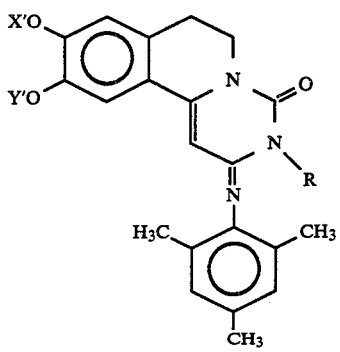

wherein one of the radicals X' and Y' denotes hydrogen and the other denotes straight-chain or branched C₁–C₄-alkyl, to react with an epihalogenohydrin of the formula III

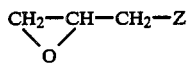

wherein Z denotes a halogen atom, such as, for example, bromine, in the presence of a base, such as, for example, potassium carbonate or sodium hydride, and a solvent, such as acetone, dimethylformamide, dimethyl sulfoxide or halogenated hydrocarbons, for example chloroform, the reaction being accelerated or completed by the application of heat, for example at the boiling point of the solvent, and comprises treating the product with a compound of the formula IV

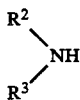

wherein R² and R³ have the abovementioned meanings, in order to obtain a compound of the formula I according to the invention.

Compounds of the formula II are advantageously prepared from the corresponding 9,10-dimethoxy derivatives (cf. German Offenlegungsschrift No. 2,720,085) by customary demethylation processes, for example treatment with hydriodic or hydrobromic acid, pyridine hydrochloride or sodium ethylmercaptide/dimethylformamide.

The compounds according to the present invention also comprise the pharmaceutically tolerated salts of the compounds of the formula I. These salts are prepared by treatment of the compounds of the formula I with an appropriate amount of a suitable acid, normally in a solvent. Examples of inorganic and organic acids which may be used have already been listed above.

The compounds according to the invention possess valuable pharmacological properties, for example, hypotensive activity, as has been shown in animal experiments. It is assumed that this hypotensive activity is the result of peripheral vasodilation, at least to some extent.

The hypotensive activity is determined by administration of a compound according to the invention to rats having spontaneous high blood pressure (SH rats) and measurement of the effect on the blood pressure.

The ability of the compounds according to the invention to decrease the blood pressure in SH rats shows that these compounds and their salts are suitable for the treatment of high blood pressure in human and veterinary medicine. The compounds according to the invention can also be employed in combination with other pharmacologically active agents, for example diuretics, cardiac vasodilators and lipid-lowering agents.

The active agents according to the invention can be administered perorally, parenterally (intramuscularly, intraveneously or subcutaneously), rectally or locally externally, optionally in the form of sprays.

The following dosages for decreasing the blood pressure are used for mammals: daily dose: from 0.1 to 200 mg, dose unit: 0.1 to 25 mg.

The new compounds can be employed either alone or mixed with pharmacologically tolerated vehicles. For oral administration, the active agents are mixed with usual substances and converted into a customary form for administration, for example, tablets, hard capsules, aqueous/alcoholic or oily suspensions or solutions. Suitable inert vehicles are, for example, magnesium carbonate, lactose or corn starch, to which their substances, such as magnesium stearate, can be added. The formulations can be prepared in the form of dry or moist granules. Oily vehicles or solvents which can be used are plant or animal oils, such as sunflower oil or cod-liver oil.

The active agents can be injected intravenously in emergencies. For this purpose, the active agents or their physiologically tolerated salts, when they are sufficiently soluble, are dissolved in usual auxiliaries, which can also serve as solubilizers or buffers.

Physiologically tolerated salts are formed, for example, with the following acids: hydrochloric acid, hydrobromic and hydriodic acid, phosphoric acid, sulfuric acid, methyl sulfuric acid, amidosulfonic acid, nitric acid, tartaric acid, lactic acid, malonic acid, fumaric acid, oxalic acid, citric acid, malic acid, mucic acid, benzoic acid, salicyclic acid, aceturic acid, pamoic acid, naphthalene-1,5-disulfonic acid, ascorbic acid, phenylacetic acid, p-aminosalicylic acid, hydroxyethylsulfonic acid, benzenesulfonic acid or artificial resins which contain acid groups, for example those with ion exchanger activity.

Suitable solvents for intravenous administration are, for example, water, physiological saline or dilute alcohols, such as ethanol, propanediol or glycerol, in addition, sugar solutions, such as glucose or mannitol solutions, but a mixture of the solvents mentioned is also suitable.

The following examples are intended to illustrate the invention in more detail:

EXAMPLE 1

9-Methoxy-10-[3'-phenylpiperazino)-2'-hydroxypropoxy]-2-mesitylamino-3-methyl-3,4,6,7-tetrahydro-2H-pyrimido(6,1-a)isoquinolin-4-one dihydrochloride dihydrate Step (a)

9-Methoxy-10-hydroxy-2-mesitylimino-3-methyl-3,4,6,7-tetrahydro-2H-pyrimido(6,1-a)isoquinolin-4-one (5.67 g) and epibromohydrin (3.03 g) were added to a suspension of anhydrous potassium carbonate (18.0 g) in dry acetone (400 ml), and the mixture was boiled under reflux for 22 hours. The reaction mixture was then filtered. Evaporation of the filtrate in vacuo produced a solid material which was crystallized from methanol. Yield 4.71 g, m.p. 171°–172° C.

Step (b)

A mixture of the product (3.22 g) obtained in step (a) in chloroform (125 ml) was treated with N-phenylpiperazine (7.2 g) and boiled under reflux for 30 hours. Excess chloroform was distilled off in vacuo. The residue was chromatographed on a silica gel column using benzene/chloroform (1:1) as eluant. Evaporation of the fractions which contained the desired product produced a solid material which was converted into its hydrochloride by treatment with ethereal hydrochloric acid in ethanol. The dihydrochloride dihydrate was crystallized from ethanol/ether. Yield 2.9 g, m.p. 208°–210° C.

EXAMPLE 2

9-Methoxy-10-[3'-(4-(2-pyridyl)piperazino)-2'-hydroxypropoxy]-2-mesitylimino-3-methyl-3,4,6,7-tetrahydro-2H-pyrimido(6,1-a)isoquinolin-4-one trihydrochloride dihydrate Step (a)
Step (a) in Example 1 was repeated.
Step (b)
The process of step (b) in Example 1 was repeated with N-(2-pyridyl)piperazine instead of N-phenylpiperazine, the trihydrochloride being obtained. Yield 74%, m.p. 195°–197° C.

EXAMPLE 3

9-Methoxy-10-[3'-(4-phenylpiperidino)-2'-hydroxypropoxy]-2-mesitylimino-3-methyl-3,4,6,7-tetrahydro-2H-pyrimido(6,1-a)isoquinolin-4-one dihydrochloride monohydrate Step (a)
Step (a) in Example 1 was repeated.
Step (b)
The process of step (b) in Example 1 was repeated with 4-phenylpiperidine instead of N-phenylpiperazine, the dihydrochloride monohydrate being obtained. Yield: 57%, m.p. 225°–229° C.

EXAMPLE 4

10-Methoxy-9-[3'-(4-phenylpiperidino)-2'-hydroxypropoxy]-2-mesitylimino-3-methyl-3,4,6,7-tetrahydro-2H-pyrimido(6,1-a)isoquinolin-4-one dihydrochloride sesquihydrate The processes of steps (a) and (b) in Example 1 were repeated, 9-hydroxy-10-methoxy-2-mesitylimino-3-methyl-3,4,6,7-tetrahydro-2H-pyrimido(6,1-a)isoquinolin-4-one being used instead of 9-methoxy-10-hydroxy-2-mesitylimino-3-methyl-3,4,6,7-tetrahydro-2H-pyrimido(6,1-a)isoquinolin-4-one in step (a) and 4-phenylpiperidine instead of N-phenylpiperazine in step (b). The dihydrochloride sesquihydrate was obtained. Yield: 60%, m.p. 171°–173° C.

We claim:
1. A compound of the formula

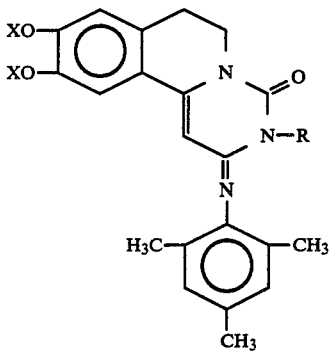

or a pharmceutically acceptable salt thereof where R is $(C_1-C_4)$-alkyl and one of X and Y is $(C_1-C_4)$-alkyl and the other is $$-CH_2CH(OR^1)CH_2NR^2R^3$$

wherein $R^1$, $R^2$, and $R^3$, taken alone, are the same or different and are hydrogen or $(C_1-C_4)$-alkyl, or $R^2$ and $R^3$, taken together with the nitrogen atom to which they are bound, are piperazino, piperidino, or piperazino or piperidino substituted by $(C_1-C_4)$-alkyl, $(C_2-C_5)$-carboalkoxy, pyridyl, phenyl, or phenyl mono-, di-, or tri-substituted by halogen, hydroxyl, methyl, ethyl, methoxy, nitro, or trifluoromethyl.

2. A compound or salt as in claim 1 wherein $R^2$ and $R^3$ are taken together and are piperazino or piperidino substituted by pyridyl or phenyl.

3. A compound as in claim 1 which is 9-methoxy-10-[3'-(4-phenylpiperazino)-2'-hydroxypropoxy]-2-mesitylamino-3-methyl-3,4,5,6-tetrahydro-2H-pyrimido-(6,1-a)isoquinolin-4-one or a pharmaceutically acceptable salt thereof.

4. A compound as in claim 1 which is 9-methoxy-10-{3'-[(2-pyridyl)piperazino]-2'-hydroxypropoxy}-2-mesitylimino-3-methyl-3,4,6,7-tetrahydro-2H-pyrimido-(6,1-a)isoquinolin-4-one or a pharmaceutically acceptable salt thereof.

5. A compound as in claim 1 which is 9-methoxy-10-[3'-(4-phenylpiperidino)-2'-hydroxypropoxy]-2-mesitylimino-3-methyl-3,4,6,7-tetrahydro-2H-pyrimido-(6,1-a)isoquinolin-4-one or a pharmaceutically acceptable salt thereof.

6. A compound as in claim 1 which is 10-methoxy-9-[3'-(4-phenylpiperidino)-2'-hydroxypropoxy]-2-mesitylimino-3-methyl-3,4,6,7-tetrahydro-2H-pyrimido-(6,1-a)isoquinolin-4-one.

7. A pharmaceutical composition for the treatment of hypertension comprising an antihypertensively effective amount of a compound as in claim 1 in admixture or conjunction with a pharmaceutically suitable carrier.

8. A method for treating high blood pressure in a patient suffering therefrom which comprises administering a said patient an antihypertensively effective amount of a compound as in claim 7.

* * * * *